(12) United States Patent
Shachaf et al.

(10) Patent No.: US 8,642,009 B2
(45) Date of Patent: Feb. 4, 2014

(54) DIAGNOSTIC SYSTEM FOR THE DETECTION OF SKIN CANCER

(76) Inventors: Catherine M. Shachaf, Palo Alto, CA (US); Amit Shachaf, Palo Alto, CA (US)

(*) Notice: Subject to any disclaimer, the term of this patent is extended or adjusted under 35 U.S.C. 154(b) by 371 days.

(21) Appl. No.: 12/097,509

(22) PCT Filed: Dec. 18, 2006

(86) PCT No.: PCT/US2006/048237
§ 371 (c)(1),
(2), (4) Date: Sep. 18, 2008

(87) PCT Pub. No.: WO2007/075565
PCT Pub. Date: Jul. 5, 2007

(65) Prior Publication Data
US 2009/0220415 A1   Sep. 3, 2009

Related U.S. Application Data

(60) Provisional application No. 60/751,440, filed on Dec. 16, 2005.

(51) Int. Cl.
*A61K 49/00* (2006.01)

(52) U.S. Cl.
USPC .......................................................... 424/9.1

(58) Field of Classification Search
None
See application file for complete search history.

(56) References Cited

U.S. PATENT DOCUMENTS

| | | | |
|---|---|---|---|
| 4,239,390 A | 12/1980 | Scherer | |
| 4,560,252 A | 12/1985 | Mori | |
| 4,786,813 A | 11/1988 | Svanberg et al. | |
| 4,870,484 A | 9/1989 | Sonehara | |
| 5,094,531 A | 3/1992 | Garner et al. | |
| 5,536,814 A | 7/1996 | Ruoslahti et al. | |
| 5,650,135 A | 7/1997 | Contag et al. | |
| 5,686,300 A | 11/1997 | Berndt | |
| 5,699,798 A | 12/1997 | Hochman et al. | |
| 5,759,996 A * | 6/1998 | Cheng et al. | 514/13.3 |
| 5,798,805 A | 8/1998 | Ooi et al. | |
| 5,981,478 A | 11/1999 | Ruoslahti et al. | |
| 6,284,223 B1 | 9/2001 | Luiken | |
| 6,512,236 B2 | 1/2003 | Seville | |
| 6,748,259 B1 | 6/2004 | Benaron et al. | |
| 7,139,598 B2 | 11/2006 | Hull et al. | |
| 7,365,844 B2 | 4/2008 | Richards-Kortum et al. | |
| 7,371,364 B2 * | 5/2008 | Li et al. | 424/1.69 |
| 7,564,550 B2 | 7/2009 | Yaroslavsky et al. | |
| 7,720,532 B2 | 5/2010 | Hashimshony et al. | |
| 2004/0220100 A1 * | 11/2004 | Waugh et al. | 514/12 |
| 2007/0255169 A1 | 11/2007 | Hashimshony et al. | |
| 2008/0267882 A1 | 10/2008 | Chen et al. | |
| 2008/0272312 A1 | 11/2008 | Tuschel | |
| 2009/0297450 A1 | 12/2009 | Ruoslahti et al. | |
| 2010/0322862 A1 | 12/2010 | Ruoslahti et al. | |
| 2011/0021908 A1 | 1/2011 | Lee et al. | |
| 2011/0059016 A1 | 3/2011 | Ramanujam et al. | |
| 2011/0064658 A1 | 3/2011 | Scherz et al. | |
| 2011/0065899 A1 | 3/2011 | Kon et al. | |
| 2011/0085974 A1 | 4/2011 | Chung et al. | |
| 2011/0104075 A1 | 5/2011 | Dmochowski et al. | |
| 2011/0117025 A1 | 5/2011 | Dacosta et al. | |
| 2011/0165075 A1 | 7/2011 | Rajopadhye et al. | |

FOREIGN PATENT DOCUMENTS

| | | |
|---|---|---|
| AU | 199863740 B2 | 6/1998 |
| EP | 0927045 B1 | 12/2005 |
| WO | WO 97/10507 A1 | 3/1997 |
| WO | 9809155 | 3/1998 |
| WO | 0125399 | 4/2001 |
| WO | 0125410 | 4/2001 |
| WO | 02080771 | 10/2002 |
| WO | 2005034926 | 4/2005 |
| WO | 2005077065 | 8/2005 |
| WO | WO 2005/072622 A1 | 8/2005 |
| WO | WO 2006/083986 A2 | 8/2006 |
| WO | WO 2006/083986 A3 | 11/2006 |
| WO | WO 2006/083986 A9 | 1/2007 |
| WO | WO 2011/072401 A1 | 6/2011 |

OTHER PUBLICATIONS

Schmieder et al., Magnetic Resonance in Medicine, Mar. 2005, 53: 621-627.*
Anikijenko, P. et al., "In Vivo detection of small subsurface melanomas in athymic mice using noninvasive fiber optic confocal imaging", Journal of Investigative Dermatology, 2001, 117(6):1442-1448.
Bussau, L. J. et al., "Fiber optic confocal imaging (FOCI) of keratinocytes, blood vessels and nerves in hairless mouse skin in vivo", Journal of Anatomy, 1998, 192:187-194.
Suihko, C. et al., "Fluorescence fiber-optic confocal microscopy of skin in vivo: microscope and fluorophores", Skin Research and Technology, 2005, 11:254-267.
Swindle, L. D. et al., "View of normal human skin in vivo as observed using fluorescent fiber-optic confocal microscopic imaging", The Journal of Investigative Dermatology, 2003, 121(4):706-712.
Cai; et al., "Multimodality tumor imaging targeting integrin alphavbeta3", Biotechniques (2005), 39(6):S14-S25.

(Continued)

*Primary Examiner* — Hong Sang
(74) *Attorney, Agent, or Firm* — Bozicevic, Field & Francis LLP; Pamela J. Sherwood

(57) ABSTRACT

Methods and compositions are provided for the analysis of skin surfaces to determine the presence of neoplastic tissue. In the methods of the invention, a composition comprising a florescent probe that binds to a specific neoplasia associated marker is applied topically to the area of interest. After topical administration, the probe preferentially binds to markers associated in neoplastic lesions in situ, which binding is detected with a compact illumination unit that provides illumination at a wavelength appropriate for image acquisition. The illumination unit comprises a light source and fiber optic bundle to direct the light towards the area of examination. A detection unit is used to capture and record an image of the area of investigation. The detection unit may be a digital camera, film camera, etc. A mapping module may also be provided to catalogue the site of examination.

17 Claims, 6 Drawing Sheets

(56) References Cited

OTHER PUBLICATIONS

Haubner; et al., "Noninvasive imaging of [alpha]v[beta]3 integrin expression using <18>F-labeled RGD—containing glycopeptide and positron emission tomography", Cancer Research (2001), 61(5):1781-1785.

Lange, "Controlled Drug Delivery in Photodynamic Therapy and Fluorescence-based Diagnosis of Cancer", Handbook of Biomedical Fluorescence (2003), Eds. Brian W. Rogue and Mary-Ann Mycek., 73 pages.

Hauser, et al. A solid-state instrument for fluorescence chemical sensors using a blue light-emitting diode of high intensity. Measurement Science and Technology. 1995; 6(8):1081-1085.

Lakowicz, J.R. Instrumentation for Fluorescence Spectroscopy. In Principles of Fluorescence Spectroscopy. Plenum Press. New York and London. Third Printing, Mar. 1986, pp. 19-27, and 32-36.

* cited by examiner

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1

Cys Asp Cys Arg Gly Asp Cys Phe Cys
1               5
```

DIAGNOSTIC SYSTEM FOR THE DETECTION OF SKIN CANCER

CROSS-REFERENCE TO RELATED APPLICATIONS

This application is a 35 U.S.C. §371 United States National Phase Application of International Application No. PCT/US2006/048237, filed Dec. 18, 2006, which claims the benefit of U.S. Provisional Application No. 60/751,440, filed Dec. 16, 2005, which application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Sep. 13, 2013, is named 37311-701.201_SL.txt and is 578 bytes in size.

FIELD OF INVENTION

This invention relates to test methods, devices and test kits for determining the presence of neoplastic cells or tissue in the skin or in proximity of the skin by using non invasive procedures.

BACKGROUND OF THE INVENTION

More than 1 million cases of basal cell or squamous cell cancer will be diagnosed annually. The most serious form of skin cancer, malignant melanoma, is expected to be diagnosed in 59,580 persons in 2005 in the US. Since 1981, the incidence of melanoma has increased approximately 3% per year. Melanoma is the most common cancer among people 25 to 29 years old. The three major types of skin cancer are basal cell carcinoma, squamous cell carcinoma, and melanoma.

Although melanoma accounts for only 4% of all dermatological cancers, it causes more than 75% of all deaths related to skin cancer (Miller and Mihm, 2006, N Engl J Med, 355, 51-65). Metastatic melanoma can spread to other organs than the skin, most commonly the lungs and liver. The survival rate for patient with metastatic melanoma is 14% and. However if malignant melanoma is diagnosed at an early stage, it can usually be cured, but melanoma diagnosed at a late stage is more likely to spread and cause death. Early detection increases 5 year survival rate from 14% to 98% for melanoma. It is therefore exceedingly important to make efforts to improve early detection of melanoma.

Examination of the Skin by Patients and General Physicians

The only and best way to detect early skin cancer is to examine the skin (Rhodes, 2006, Dermatol Ther, 19, 50-69). Periodic self-examination of the skin, and examination of the skin is potentially life saving. A single case-control study has demonstrated a 63% reduction in mortality associated with monthly skin self-examination (Berwick, Begg, Fine, Roush and Barnhill, 1996, J Natl Cancer Inst, 88, 17-23). The prevalence of whole-body skin self-examination is relatively low even among populations at very high risk for skin cancer. Even more disappointing than the total lack or infrequent use of self-examination for suspicious skin lesions among lay persons is the relatively low frequency of whole-body skin examinations by primary practice physicians, or physician recommendations to patients that they self-examine their skin for suspicious lesions (Friedman, Whitaker-Worth, Grin and Grant-Kels, 2004, Cutis, 74, 305-11, Weinstock, Martin, Risica, Berwick, Lasater, Rakowski, Goldstein and Dube, 1999, Am J Prev Med, 17, 169-75). Skin awareness, self-examination of the skin, examination of the skin and physician examination of the skin are intervention strategies that are likely to have immediate positive impact on skin-cancer—specific mortality. Skin self-examination and examination by family members are likely to enhance the possibility of early diagnosis given the fact that patients or acquaintances suggest the diagnosis of skin-cancer about 75% of the time, whereas physicians suggest the diagnosis only 25% of the time (Epstein, Lange, Gruber, Mofid and Koch, 1999, Jama, 281, 640-3). Thus, examination of the skin at periodic intervals is central to any intervention program to reduce skin-cancer—specific mortality (Rhodes, 2006, Dermatol Ther, 19, 50-69).

The common scenario for skin cancer detection in 75% of the cases is primary detection by the individual, who then approach a health professional for opinion and evaluation. The health professional will examine skin by eyeballing or if available by dermoscopy in an attempt to properly access the presence of cancer cells (Bauer, Blum, Strohhacker and Garbe, 2005, Br J Dermatol, 152, 87-92). If he or she suspects cancer, a biopsy of the affected skin is needed to make a diagnosis. For this, the health professional will remove a sample of tissue, and a pathologist will examine it under a microscope to check for cancer cells. Currently 30 moles are removed per malignant mole for diagnostic purposes of skin cancer lesions. Methods to improve the evaluation of the neoplastic properties of melanoma cells and reduce unnecessary excision of benign melanocytic naevi are needed.

Current Methods of Detection of a Skin Cancer

Melanoma is a usually fatal skin cancer, unless it is detected and surgically removed in its earliest stages. Early detection of malignant melanoma is difficult because early melanomas, those having a Breslow thickness less than 1 mm, share many diagnostic features with benign lesions, such as dysplastic nevi or atypical melanocytic nevi.

Detection of a skin cancer such as melanoma is typically carried out by physical examination of the skin followed by biopsy of selected lesions suspected to be cancerous. The effectiveness of this procedure is dependent on the experience of the examiner, and errors in diagnosis can be fatal. Occasionally, cancers have remained undetected which metastasize beyond the original site of occurrence and lead to a decrease in survival. On the other hand a 30 fold biopsies of skin lesions occur which are not cancerous. Thus high frequencies of unnecessary surgical procedures occur. On several occasions the biopsy is carried out in the skin of the facial region and may result in some incidents of cosmetic scarring.

When an individual is diagnosed with skin cancer the physician determines if the cancer can be removed by surgery. Individuals with local disease may be cured by complete resection of the tumor. Prior to the surgery, evaluation of the spread of the tumor is conducted using X-rays, CT scans, MRI scans or PET images. These tests provide guidance prior to the surgery. During surgery, the surgeon relies on the evaluation of the pathologist to determine, real time the spread of the cancer. This procedure requires a highly trained pathologist to be present at the surgery and to rapidly analyze the tissue sample while the patient remains on the operating table. If the cancer has a great spread than anticipated, the surgeon continues to try to remove any residual tumor cells from the site intervention. In 15-25% of the incidents, residual diseased cells may remain on site in the patient. These individuals have a lower survival rate greater than those that have the tumor completely removed.

Several approaches using radioactive isotopes or photosensitizers linked to targeting entities have been conducted to determine the spread of the lesion. These detection methods are limited and cannot be used by the general physician's practice for screening individuals nor can they be used to determine the extent of the cancer lesion. Some detection methods are described in U.S. Pat. Nos. 6,256,530, 6,091,985, 6,083,487; EP patent publication No. 0588994 A1.

SUMMARY OF THE INVENTION

Methods and compositions are provided to reliably diagnose malignant and benign lesions on the surface of the body in a non-invasive manner, e.g. without oral consummation or injection into the blood stream of a diagnostic agent; without biopsy, etc. The diagnostic methods of the invention are based on florescence imaging of an externally applied florescent probe that specifically interacts with a neoplasia associated marker and thus which distinguishes between malignant and benign lesions on the surface of the body. Markers of interest include markers expressed on neoplastic cells, markers selectively expressed on neoplastic cells, markers expressed on cells associated with tumor angiogenesis; markers secreted by neoplastic cells; and the like, particularly cell surface or secreted markers. The tool is useful for home-use, e.g. by a non-professional individual, for the use in the clinic by a health professional individual; etc. In some embodiments, use by a non-professional can determine if the area on the surface of the body requires additional assessment by a health care professional. A benefit of the invention is a reduction in surgical interventions to determine if a lesion is pathological.

In the methods of the invention, a fluorescently labeled probe that specifically binds to a neoplastic marker is topically administered to a lesion suspected of being neoplastic. In some embodiments, the probe is administered in a formulation that enhances transdermal penetration, e.g. in a formulation comprising dimethyl sulfoxide (DMSO). Markers of interest include, without limitation, integrin $\alpha v \beta 3$ and/or integrin $\alpha 5 \beta 1$. After topical administration, the probe preferentially binds to markers present in neoplastic lesions, which binding is detected with a compact illumination unit that provides illumination at a wavelength appropriate for image acquisition. Positive and/or negative control probes may also be used. The imaging unit may comprise a detection unit, e.g. a camera, digital recording, etc. which records an image of the illuminated lesion. The recording may be analyzed by the patient, sent off site for analysis, analyzed by a health care professional, and the like.

In some embodiments, a system for non-invasive diagnosis of neoplastic skin lesions is provided. The system comprises a compact illumination unit that provides illumination at a wavelength appropriate for image acquisition of a fluorescent probe; and a detection unit that receives the light emitted by the surface under investigation to provide a recording of the data. Optionally, the system further comprises a topical formulation comprising a diagnostically effective dose of a fluorescently labeled probe that specifically binds to a neoplastic marker. The fluorescently labeled probe may be provided in an excipient that enhances transdermal penetration. Optionally, the system further comprises an imaging unit that can capture and/or develop the image generated from the surface under investigation.

In one embodiment, the detection unit is designed for use by a non-professional, for example in the privacy of their home, and is operable by an individual, or by an additional non-professional or professional individual. In another embodiment, the detection unit is designed for use by a health care professional.

In one embodiment, the reading and translation of the results of the image capture and detection may be done by a non-professional or a professional individual.

The invention provides a rapid evaluation tool to quickly analyze multiple skin lesions in a short time period, as well as in a non-invasive manner, to assess which lesions express markers associated with neoplasia. Additional options provide mapping of lesions, which may be archived for follow up screens to determine progression of growth.

DETAILED DESCRIPTION OF THE INVENTION

Figure 1:
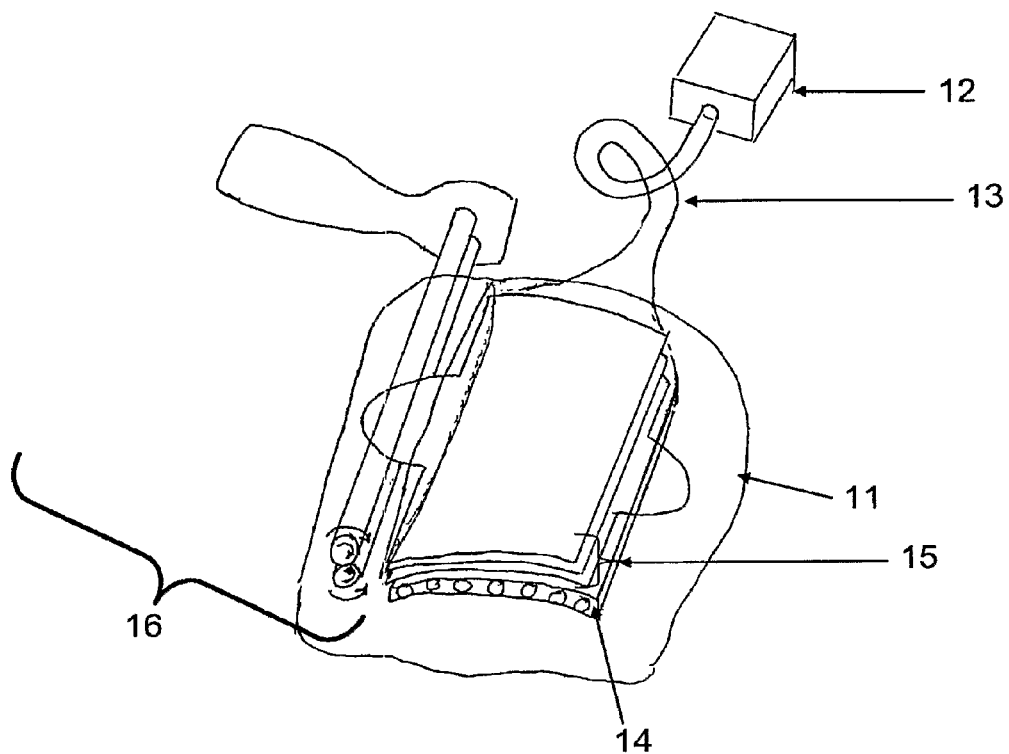
FIG. 1: is an overall schema of the flexible imaging device that may be a flexible camera, showing the adhesive unit 11, illumination source 12, the optical fiber bundle 13; the illumination unit 14; flexible image acquisition unit 15; and film pulling device 15.

The present invention provide methods for identifying, characterizing and distinguishing between non-malignant and malignant skin lesions. In the methods of the invention, a fluorescently labeled probe that specifically binds to a neoplasia associated marker is topically administered to a lesion suspected of being neoplastic. In some embodiments, the probe is administered in a formulation that enhances transdermal penetration, e.g. in DMSO. Neoplasia associated markers of interest include, without limitation, integrin αvβ3 and/or integrin α5β1. The probe preferentially binds to markers present in neoplastic lesions, which binding is detected with a compact illumination unit that provides illumination at a wavelength appropriate for image acquisition.

Before the present compositions and methods are described in further detail, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range. As used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Definitions

The term "melanoma" refers to neoplastic growth occurring in melanocytes (pigment cells). A melanoma may visually resemble a harmless mole.

The term "melanocytic nevi" or "mole" refers to the state where proliferation occurs in the pigment cells in the skin, melanocytes to generate structures that are non-characteristic for the skin. Moles may be flat or protruding. They vary in color from pink flesh tones to dark brown or black.

As used herein, the term "diagnosis" means detecting a disease or disorder or determining the stage or degree of a disease or disorder. The term "diagnosis" also encompasses detecting a predisposition to a disease or disorder, determining the therapeutic effect of a drug therapy, or predicting the pattern of response to a drug therapy or xenobiotics. The diagnosis methods of the present invention may be used independently, or in combination with other diagnosing and/or staging methods known in the medical art for a particular disease or disorder.

Thus, in one embodiment, the method of diagnosis is conducted by detecting, in a patient, the presence of one or more neoplasia associated proteins. The localization of such proteins in a lesion is indicative that such a lesion is neoplastic or pre-neoplastic.

A "kit" may be used for conducting, the diagnosis methods of the present invention. Typically, the kit should contain, in a carrier or compartmentalized container, reagents useful in any of the described embodiments of the diagnosis method. The carrier can be a container or support, in the form of, e.g., bag, box, tube, rack, and is optionally compartmentalized. The carrier may define an enclosed confinement for safety purposes during shipment and storage. In one embodiment, the kit includes a probe selectively reactive with a protein complex at the site of investigation. The probe may be labeled with a detectable marker such as fluorescence markers or enzymatic molecules or calorimetric molecules. The kit optionally comprises the image acquisition device, and may optionally further comprise reagents for preparation of the site of analysis, e.g. cleaning surfactants, etc. The kit may further comprise positive and/or negative control probes. Instructions for using the kit or reagents contained therein may also be included in the kit and instructions how to contact a health professional that will assist in analyzing the data acquired by the kit. The kit may include prepaid envelopes addressed to a diagnostic lab where analysis of the image may be conducted.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

The term "protein fragment" as used herein means a polypeptide that represents a portion of a protein. When a protein fragment exhibits interactions with another protein or protein fragment, the two entities are said to interact through interaction domains that are contained within the entities.

As used herein, the term "domain" means a functional portion, segment or region of a protein, or polypeptide. "Interaction domain" refers specifically to a portion, segment or region of a protein, polypeptide or protein fragment that is responsible for the physical affinity of that protein, protein fragment or isolated domain for another protein, protein fragment or isolated domain.

The term "antibody" as used herein encompasses both monoclonal and polyclonal antibodies that fall within any antibody classes, e.g., IgG, IgM, IgA, or derivatives thereof. The term "antibody" also includes antibody fragments including, but not limited to, Fab, F(ab').sub.2, and conjugates of such fragments, and single-chain antibodies comprising an antigen recognition epitope. In addition, the term "antibody" also means humanized antibodies, including partially or fully humanized antibodies. An antibody may be obtained from an animal, or from a hybridoma cell line producing a monoclonal antibody, or obtained from cells or libraries recombinantly expressing a gene encoding a particular antibody.

The term "compound" as used herein encompasses all types of organic or inorganic molecules, including but not limited proteins, peptides, polysaccharides, lipids, nucleic acids, small organic molecules, inorganic compounds, and derivatives thereof.

The term "specific binding member" or "binding member" as used herein refers to a member of a specific binding pair, i.e. two molecules, usually two different molecules, where one of the molecules (i.e., first specific binding member) through chemical or physical means specifically binds to the other molecule (i.e., second specific binding member). The complementary members of a specific binding pair are sometimes referred to as a ligand and receptor; or receptor and counter-receptor. For the purposes of the present invention, the two binding members may be known to associate with each other, for example where an assay is directed at detecting compounds that interfere with the association of a known binding pair. Alternatively, candidate compounds suspected of being a binding partner to a compound of interest may be used.

The term "reusable" as used herein relates to items that can be utilized several times and maintaining similar quality as when used the first time.

The term "flexible" relates to the ability of substances and items to not be rigid or any material that will enable the image acquiring device to adjust to changes in the topography of the body.

The term "flexible camera" relates to an image acquisition device that acquires images and is bendable to assume the curvatures of the body surface.

Integrins are known to be biomarkers in cancer due to their expression on endothelial and/or smooth muscle cells of blood vessels in association with tumor angiogenesis. Angiogenesis is required for the growth and maintenance of solid tumors and metastases. New blood vessels provide oxygen, nutrients and a passage for metastatic cells to enter the blood system and establish metastatic disease in a growing tumor.

The alpha v beta 3 integrin is an endothelial cell receptor for von Willebrand factor, fibrin, fibrinogen, and fibronectin, and a marker of angiogenic vascular tissue. It is expressed in the vasculature of several cancers, including skin cancers. Monoclonal antibodies to alpha v beta 3 integrin, as well as cyclic peptide inhibitors, disrupt angiogenesis and promote tumor regression (see Brooks, Clark and Cheresh, 1994, Science, 264, 569-71, Brooks, Montgomery, Rosenfeld, Reisfeld, Hu, Klier and Cheresh, 1994, Cell, 79, 1157-64).

The conserved amino acid peptide sequence, arginine-glycine-aspartic acid (RGD) is an evolutionarily conserved feature of many natural integrin-binding ligands. Peptides containing cyclic-RGD domains can bind to integrins with higher affinities than linear peptides (Koivunen, Wang and Ruoslahti, 1995, Biotechnology (N Y), 13, 265-70). Multiple copies of a cyclic RGD peptide are internalized efficiently by cells in tissue culture in an integrin-mediated manner (Hart, Knight, Harbottle, Mistry, Hunger, Cutler, Williamson and Coutelle, 1994, J Biol Chem, 269, 12468-74). The three-amino-acid sequence RGD (Arg-Gly-Asp) motif (Ruoslahti, 1996, Annu Rev Cell Dev Biol, 12, 697-715, Pasqualini, Koivunen and Ruosiahti, 1997, Nat Biotechnol, 15, 542-6) binds to integrins.

DETAILED DESCRIPTION OF THE DRAWINGS

Shown in FIG. 1, a flexible image acquiring device consisting of multiple modules will be used to acquire images of the florescent probe bound to the lesion. The illumination module 12-14, also explained in greater detail below, consists of the illumination source 12 that transports light through the fiber optic bundle 13 to the fiber optic net 14. Light will illuminate the object under investigation where the probe is applied. Light emitted from the probe will be reflected back to the image acquiring device, shown as a "flexible camera" 15. The film pulling device will facilitate the spreading of the film development solution, as is explained in greater detail below. In another, variation the image acquiring element may be a digital camera, and the like.

Figure 2:
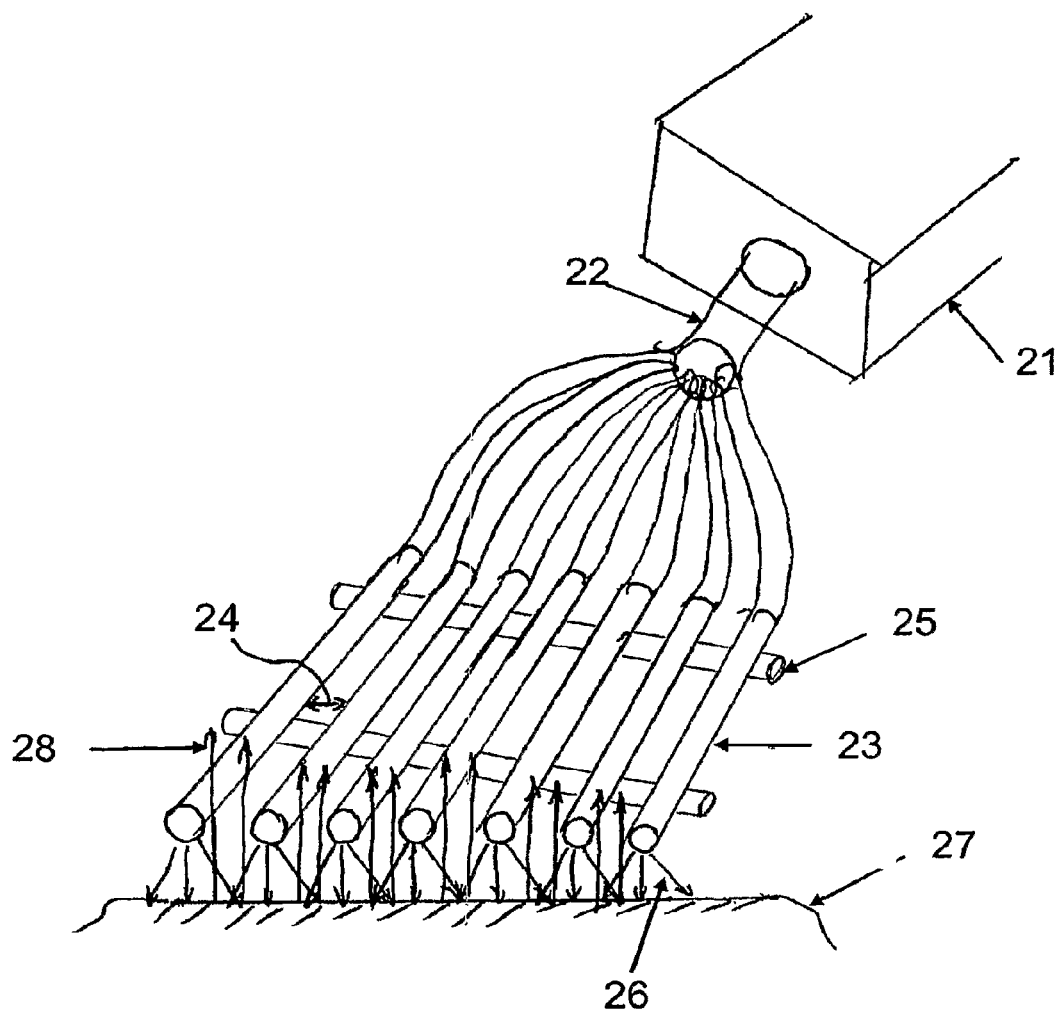
FIG. 2 shows the illumination module, where 21 represents the illumination box that includes: power, laser diode and electronic circuit; 22 is the fiber optic bundle that transfers the light to the illumination layer; 23 are flexible fiber optic rods that let the light leak from the side to illuminate the skin lesion; 24 represent the gap between the rods to let the emitted light from the skin to pass to the film; 25 represent the fiber support; 26 represents the light traveling out from the fibers; 27 represents of the body surface where the object of investigation is located and 28 represents the light emitted from the body surface under investigation.

Shown in FIG. 2 is the illumination unit consisting of the illumination box 21, which contains a switching power supply for a laser diode and may also include electronic circuits to time the exposure of the camera concurrent with the light emission. The exposure may be stopped by simultaneously stopping the light source together with the light emission. The light passages through an optic fiber bundle 22. The fibers in the fiber bundle may be of transparent polymer fibers or glass and may be 10-500 µm in diameter. The extension of the fiber optic bundle is arranged to form a flat net compromising the illumination unit of fiber optic rods 23 covering an area of 1 to 100 $cm^2$. The fibers are generally spread out in a single layer of fibers with gaps between the fibers 24. The distance between the fibers is dependent on the diameter of the fiber and may vary in spacing from 1 to 10 fiber diameter. The fibers may comprise an adhesive on the upper side. The fibers are equally spaced creating a fiber net. A sparsely placed cross section of fibers 25 consisting of 2 or more fibers that is 25% or less of the amount of fibers in the fiber net, is placed on the adhesive as support to the fiber net. The distance between the support fibers measure 5 to 20 fiber diameters. A fiber bundle and fiber net is commercially available, e.g. Schott North America Inc, etc. The cross section of fibers 25, creates a fixed spacing between the illumination fibers towards the lesion. The surface that will be illuminated may range from 1 $cm^2$ to 100 $cm^2$. The bottom of the illumination fibers may be scored or scraped to generate scratches of arbitrary or defined sizes that allow the light traveling in the fibers to leak in a unidirectional manner 26 along the fiber towards the surface of examination 27. The excitation light 26 that leaks from the optical fiber net to the lesion will excite the fluorophore label attached to the probe. The light entering the fibers range from about 0.01-10 W. The probe that reacts with its target in the lesion will emit fluorescent light that correlates to the emission spectra of the fluorophore attached to the probe. The emitting light will be reflected back through the gaps between the fibers towards the image acquiring device placed above the illumination bundle. In an alternative embodiment, organic light emitting diodes (OLED) or ceramic diodes printed on a flexible transparent surface with spaces of 1 to 10 diode width are used as an illumination unit.

Figure 3:
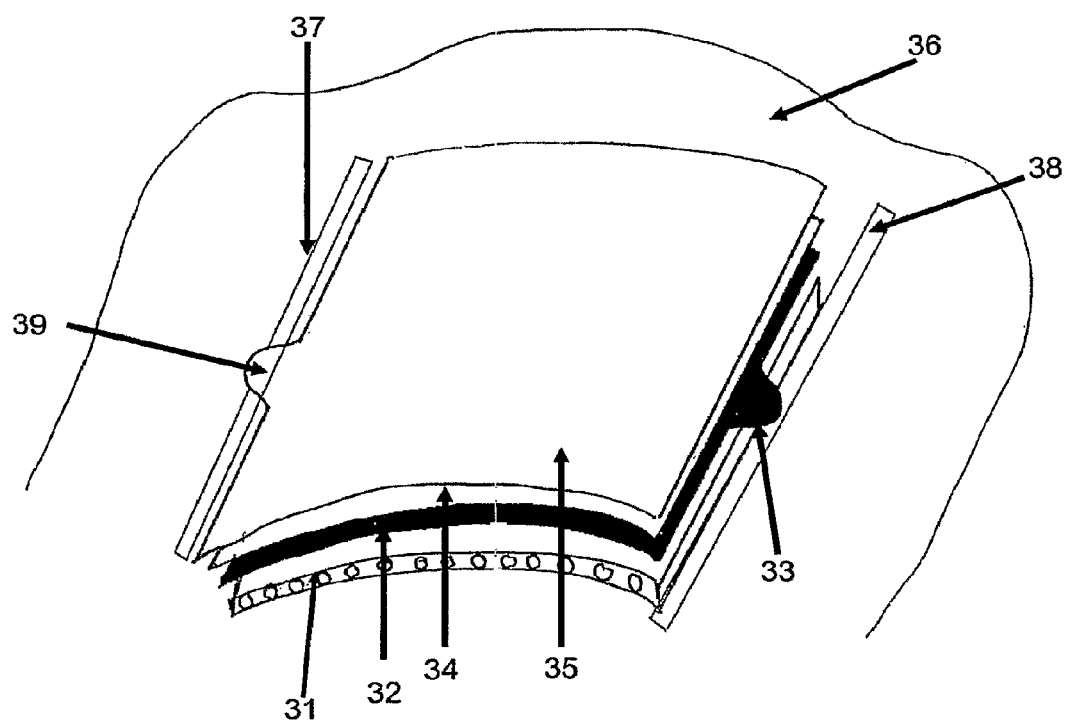
FIG. 3 shows the schema for the flexible image acquisition device or the "flexible camera", where 31 represents the illumination unit of optical fibers; 32 represent an opaque black sheet; 33 represents a flap; 34 represents a filter band layer—Flexible emission filter/band pass filter; 35 represents an instant development film; 36 represents a non transparent adhesive material that covers the device to prevent outside light to enter the imaging module; 37 represents a slit that allows the removal of 32 and 38 is a slit that allows the removal of 35 using a flap 39.

The image acquisition device may be a "flexible, camera" indicated in 15 and detailed in FIG. 3. The flexibility of the imaging acquisition module allows image acquisition of the non-level body surfaces. The illumination unit containing the fiber optic net 31, is at the bottom and is adjacent to the body area under investigation. At the bottom of the image acquisition device and above the illumination unit 31 is an opaque sheet 32. This sheet keeps the film dark until ready for exposure. The opaque sheet is removable following placement of the imaging module on the area of investigation and has a flap 33 that will allow gripping, pulling and removal. The next module is a flexible emission filter 34. The filter is custom designed and made of thin transparent flexible polymers and coated with inorganic or organic filtering materials. The filter is transparent to light emitted from the label. This filter may be manufactured but not limited, by SimiChroma Technology Corp. The light will hit the photosensitive surface of an instant development film 35 (for example Polaroid corporation film) 35. The sensitivity of the film may range from 400-1600 ASA. The uppermost layer of the flexible camera is an adhesive opaque adhesive material that covers the entire imaging module while protecting it from outside light 36. This layer has 2 openings/slits. Slit 37 allows the removal of opaque sheet 32 by pulling the flap 33 and slit 38 that allows for the removal of the film 35 by pulling at the flap 39.

The adhesive unit 36 adheres to the surface of the body surface, preferably with the aid of a removable adhesive. Particularly suitable are adhesive tapes that allow fixation of the attachment device on the tissue, e.g. of human skin, over a period of several minutes up to an hour. Moreover, it is also preferred that the adhesive used can be more easily removed from the surface of the tissue after wearing than from the surface used for fixing it to the attachment device. This is possible with the adhesive given in the above example. The adhesive used to link the Image acquisition device to the tissue surface should also exhibit light absorbing properties. Advantageously, the invention avoids that light from the environment arrives at skin areas that are directly adjacent to the image acquisition device. It is particularly preferred that the outer diameter of the adhesive tape be slightly larger than the diameter of the attachment device. The areas of the adhesive tape which are not covered by the attachment device are preferably covered with a protective film that is opaque to light or are impregnated with a dye that is opaque to light in order to prevent external light from entering the measurement area or to reduce this effect as far as possible. The adhesive should be selected such that it exhibits none or only very little reflection at its inner surfaces. A lateral transport of light caused by reflection at the inner surfaces or by in homogeneities in the adhesive should be avoided in order to prevent cross talk between emitter and receiver by the adhesive. The adhesive is selected such that the loss of light is as small as possible when light is traveling through. Such adhesive tapes are commonly known. The double-sided polyester adhesive tape manufactured by Adhesives Research (Art. No. AR 8254) based on acrylic glue is suitable.

Figure 4:
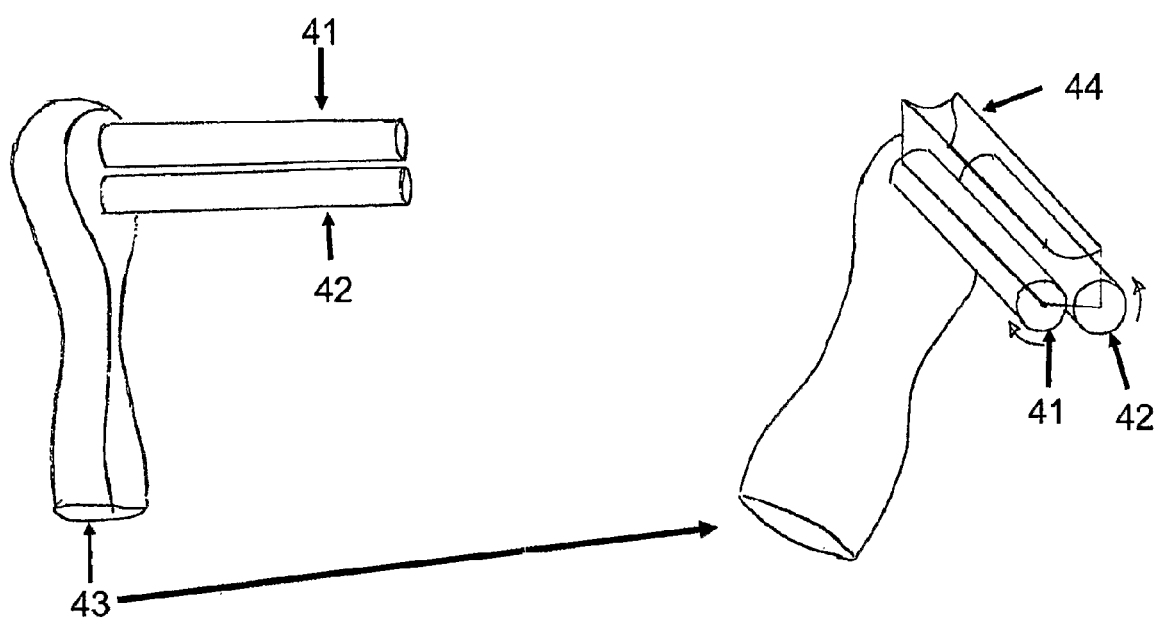
FIG. 4 shows a film pulling device, where 41 represents one of two rollers and 42 represents the second roller presses the film when pulled; 43 represents a handle with a motor for the user to hold and 44 is a light protective sleeve.

Shown in FIG. 4, is the film pulling device. Spacer rollers 41 and 42 are adhered on both sides of the photosensitive film sheet 35. A DC motor is enclosed in the handle of the device 43 to firmly press the development solution to the photoreactive surface while the film is pulled through the rollers. The squeezing of film through the motorized pulling device rollers evenly spreads the developing solution to initiate the development of the film, using a methodology similar to that of a Polaroid camera. A opaque sleeve 44 prevents light from outside sources to react with the photoreactive surface before it interacts with the development solution and covers the slit 37.

Figure 5:
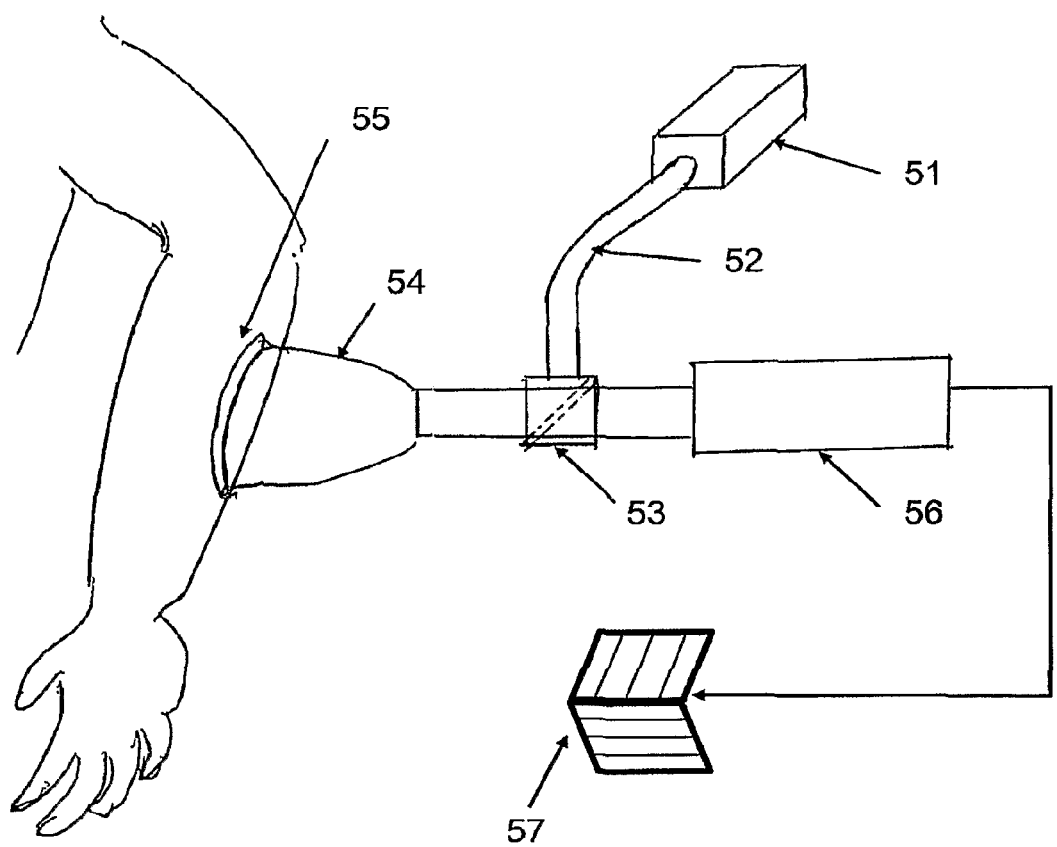
FIG. 5 shows a schema for the non flexible imaging device, where 51 represents the illumination source; 52 represents the fiber optic bundle for transferring the illumination; 53 represents the fluorescence cub (lens, one excitation filer directional mirror and emission filter); 54 represents a flexible hood to cover the object and the lens from external illumination; 55 represents the body surface with the lesion to be inspected and 56 represents an image acquisition device and 57 represents a data recordation device.

An alternative image acquisition device is shown in FIG. 5. Light is transmitted from a illumination box 51. Light is transmitted from the illumination box 51 contains a light source that may be and not limited to a xenon lamp or a diode. Any convenient source may be used, for example Prior Scientific Lumen 200 Fluorescence Illumination System. The light is transmitted through a fiber optic bundle 52 to a fluorescence beam splitter cube 53. The beam splitter cube will contain an excitation light filter between the light beam from the illumination cube and an emission filter between the light emitted from the body surface to the camera. The filters can be pulled away from the light beam in the cube to allow acquisition of bright-field images. The beam splitter cube projects the beam towards the object of investigation between the light beam from the illumination cube and an emission filter between the light emitted from the body surface to the camera. Fluorescence cubes are commercially available from several vendors (Nikon, Leica). A camera lens hood 54 made of dark, opaque material generates local darkness for optimal light measurements. The camera lens hood determines the distance from the illumination cube and the camera, to the object under investigation 55 while sealing the area of investigation from outside light. Emitted light from the object of investigation will travel to the image acquisition device 55. The image acquisition device may be a digital camera 56. The camera may be a 12 bit digital output with low read noise and detection that may be 1×1 pixels. The digital camera may contain a lens to allow enlargement of the image from 0.2 to 2 fold magnification. The camera may acquire flouresence light emitted from the body surface and acquire the bright-field image of the surface of the area under investigation. Various digital cameras may be used, for example the Retiga EXi manufactured by QImaging. The camera may have an internal display or connected to a data recording device 56 that will display the image. A software program may be used to analyze the images.

Figure 6:
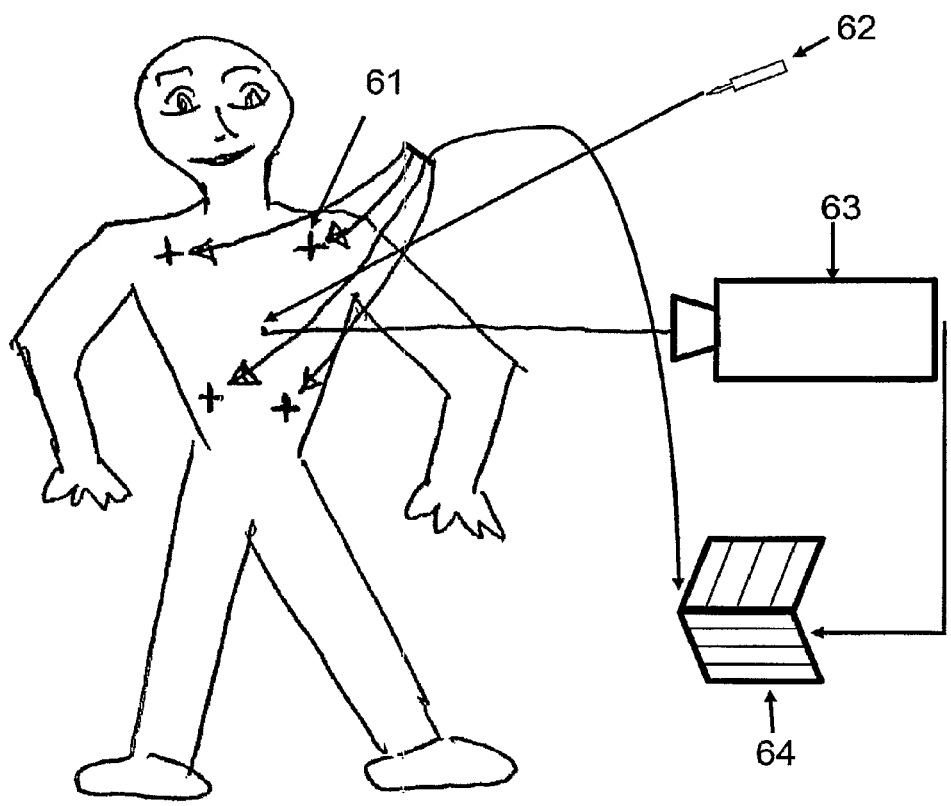
FIG. 6 shows the body mapping device to locate and track lesions on a specific location on the body, where 61 represents optical light-emitting diodes as markers/sensors applied to the patient body—"the body coordinate markers; 62 represent a laser marker to mark the position of the mole under inspection for the camera—the "lesion marker"; 63 represents an image acquiring device and 64 a data recordation device.

FIG. 6 illustrates a mapping module 61-63 to map the lesion on body coordinates. Pluralities of high intensity LED (light emitting diode) markers are placed on specific body coordinates. These are the "body coordinate markers". The markers emit light at any wavelength convenient for detection, e.g. from around about 400 to around about 600 nm, usually around about 500 nm, e.g. about 520 nm. Similar LED markers may be purchased from Wabash National, L.P. These body coordinates are permanent coordinates that can be reliably located at a later time point. For example, see Taneji, 2006, Electro-Optical and Infrared Systems: Technology and Applications III, Proceedings of SPIE—Volume 6395, 639510/1-8. These coordinates may be but not limited to; ears; nose; elbow; nipple; belly button; shoulder bone; rib; etc. An additional laser beam 62 emitting light at a wave length different than the markers, from a hand held source maybe but not limited to a wave length of 650 nm. This is the "lesion marker", which maybe but not limited to GLP3; available from manufacturer Roithner Laser Technik. The wavelengths of the light are chosen so that a color camera can distinguish the color of the coordinate markers from the lesion marker. The body coordinate markers maintain the coordinates of the body while the lesion marker locates the lesion on the body. An image acquisition device 63 acquires images of the location of the lesions by manually targeting the lesion under investigation together with the body coordinate markers. Image acquisition devices of interest include digital cameras, which may comprise a charge-coupled device (CCD) sensor or complementary metal-oxide-semiconductor (CMOS). An example of this camera may be "Retiga SRV" available from QIMAGING. The body coordinate markers and the image acquisition device are connected to a data recording device 64 that enables storage of the body coordinates and lesion marker and images of the lesion. A software or hardware program in the data recording device, analyzes the location of the lesion coordinates in comparison to the body coordinate markers. A data analysis device generates a projection of 3D information positioning the lesion under investigation on the body in reference to the position of each body coordinate marker. In addition, data of the fluorescent images of the probe and bright light images of the lesion may also be referenced to the coordinate data of the lesion.

Diagnostic Methods

The diagnostic methods of the invention are based on florescence imaging of an externally applied florescent probe that specifically interacts with a neoplasia associated marker and thus which distinguishes between malignant and benign lesions on the surface of the body. Markers of interest include markers expressed on neoplastic cells, markers selectively expressed on neoplastic cells, markers expressed on cells associated with tumor angiogenesis; markers secreted by neoplastic cells; and the like, particularly cell surface or secreted markers. Optionally the marker is compared to a negative and/or positive control, e.g. a fluorophore in the absence of a binding probe as a negative control; and the like. Alternatively, optional instructions depicting positive and negative images may be included in kits of the invention.

In the methods of the invention, the fluorescently labeled probe is topically administered to a lesion suspected of being neoplastic. In some embodiments, the probe is administered in a formulation that enhances transdermal penetration. After topical administration, the probe preferentially binds to markers present in neoplastic lesions. The probe for detection can be a peptide, antibody, aptamer, peptoid, DNA or RNA that recognizes and specifically binds to a specific epitope or nucleic acid that distinguishes neoplastic tissue form normal tissue when topically applied. In some embodiments, the probe is a peptide or protein fragment, including a cyclic peptide. In other embodiments the probe may be a combination of more than one peptide or protein or protein fragments. In other embodiments the probe is an antibody or fragment thereof. In another embodiment, the probe is an aptamer or peptoid.

In the method of detection, the probe may be directly conjugated to a fluorophore; or to a tandem fluorescent peptide or protein construct comprising of specific binding members, a donor fluorescent protein moiety and an acceptor fluorescent moiety. The said acceptor fluorescent protein moiety exhibits fluorescence resonance energy transfer when said donor fluorescent protein moiety is excited, and donor fluorescent protein moiety, contacting first donor fluorescent protein to emit detectable fluorescence.

Markers of interest, also referred to as biomarkers, include protein, lipids, DNA or RNA that are expressed by neoplastic or angiogenic cells, preferably selectively expressed by neoplastic or angiogenic cells. In some embodiments, the marker is a cell surface or secreted polypeptide. The term "selective" expression refers to a level of expression when compared to surrounding tissue, e.g. surrounding skin tissue, where the concentration of the marker is increased at least about 2-fold, at least about 5-fold, at least about 10-fold or more in neoplastic or angiogenic cells when compared to surrounding normal tissues. It will be understood by one of skill in the art that a marker may be selectively expressed in skin cancer cells, and still be highly expressed in unrelated tissues, e.g. in embryonic tissues, none-skin tissues, and the like. Neoplastic markers useful in the detection of neoplastic cells include, without limitation, the following markers.

Integrin $\alpha v\beta 3$ is of interest as a marker. Integrins are heterodimeric transmembrane receptors. Integrin alpha(v)beta (3) is an adhesion molecule involved in tumor invasion, angiogenesis, and metastasis. The expression of the beta3 integrin subunit expression is high in the tumorigenic or vertical growth phase compartment of many primary melanomas and in most metastatic melanomas. Integrin, alpha V is a vitronectin receptor, alpha polypeptide (antigen CD51)—which sequence is known in the art and publicly available, for example GenBank accession number NM_002210. Integrin, beta 3 is a platelet glycoprotein IIIa (antigen CD61)—which sequence is known in the art and publicly available, for example GenBank accession number NM_000212. Description of the proteins may be found in, for example, Felding-Habermann, Mueller, Romerdahl and Cheresh, 1992, J Clin Invest, 89, 2018-22, Van Belle, Elenitsas, Satyamoorthy, Wolfe, Guerry, Schuchter, Van Belle, Albelda, Tahin, Herlyn and Elder, 1999, Hum Pathol, 30, 562-7, Wang, Wu, Pasuelo, McMurray and Li, 2005, Bioconjug Chem, 16, 729-34, each herein specifically incorporated by reference with respect to the teaching of these proteins.

Integrin $\alpha 5\beta 1$ is of interest as a marker. The integrin $\alpha_5$ subunit predominantly couples with $\beta_1$ subunit, and is a receptor for fibronectin. This integrin is one of representative ECM receptors and has particularly important roles in tumor growth invasion and malignant behavior. It only interacts with fibronectin and is elevated in highly metastatic melanoma. Integrin, alpha 5 is a fibronectin receptor, alpha polypeptide—which sequence is known in the art and publicly available, for example GenBank accession number NM_002205. Integrin, beta 1 (fibronectin receptor, beta polypeptide, (antigen CD29 includes MDF2, MSK12)—which sequence is known in the art and publicly available, for example GenBank accession number NM_002211. Description of the proteins may be found in, for example, Nesbit and Herlyn, 1994, Invasion Metastasis, 14, 131-46, herein specifically incorporated by reference with respect to the teaching of these proteins.

CD34 is of interest as a marker. It is a hematopoietic stem cell antigen expressed in bone marrow and endothelial cells, and in vascular and spindle cell tumors. The protein sequence is known in the art and publicly available, for example GenBank accession number NM_001773. Description of the protein may be found in, for example, Breza and Magro, 2005, J Cutan Pathol, 32, 685-9 herein specifically incorporated by reference with respect to the teaching of the protein.

MCAM/MUC18 is of interest as a marker. The cell surface glycoprotein MUC18 precursor (Melanoma-associated antigen MUC18) antigen is an integral membrane glycoprotein of 113 kDa whose expression on primary human melanomas correlates with poor prognosis and the development of metastatic disease. The protein sequence is known in the art and publicly available, for example GenBank accession number NM_000247. Description of the protein may be found in, for example, Shih, Elder, Hsu and Herlyn, 1994, Am J Pathol, 145, 837-45 herein specifically incorporated by reference with respect to the teaching of the protein.

ICAM is of interest as a marker. In the transformation from benign to malignant neoplasms, the expression of ICAM-1 was upregulated strongly. The protein sequence is known in the art and publicly available, for example GenBanki accession number NM 000201. Description of the protein may be found in, for example, Natali, Hamby, Felding-Habermann, Liang, Nicotra, Di Filippo, Giannarelli, Temponi and Ferrone, 1997, Cancer Res, 57, 1554-60, van Duinen, van den Broek, Vermeer, Fleuren and Bruijn, 1994, Cancer, 73, 2131-9 herein specifically incorporated by reference with respect to the teaching of the protein.

MAGE is of interest as a marker. The melanoma antigen family (MAGE) is expressed in melanocytic tumors and is restricted to invasive malignant tumors and absent in nevi. The protein sequences are known in the art and publicly available, for example GenBank accession numbers NM_004988, NM 021048, NM 005366, NM_005367, NM_175743, NM_005362, NM_002362, NM_021049, NM_175868, NM_005364, NM_005365, NM_177415, NM_182506, NM_173699, NM_002364, NM_002365, NM_002367, XM_293407, NM_005462, NM_016249, NM_177456, NM_006986, NM_177433, NM_177537, NM_020932, NM_020932, NM_138703, NM_022149, NM_014061, NM_019066. Description of the proteins may be found in, for example, Busam, Iversen, Berwick, Spagnoli, Old and Jungbluth, 2000, Mod Pathol, 13, 459-65 herein specifically incorporated by reference with respect to the teaching of the proteins.

TNF α/β is of interest as a marker. TGF α/β proteins are a biological marker of melanoma progression in situ and correlate with expression of a marker of proliferation, Ki67, and with beta 3 integrin subunit expression. The protein sequence is known in the art and publicly available, for example GenBank accession number NM_021578, NM_003236. Description of the protein may be found in, for example, Moretti, Pinzi, Berti, Spallanzani, Chiarugi, Boddi, Reali and Giannotti, 1997, Melanoma Res, 7, 313-21 herein specifically incorporated by reference with respect to the teaching of the protein.

uPA is of interest as a marker. Plasminogen activators provide tumor cells with efficient means to degrade extracellular matrix constituents and thereby facilitate their dissemination to distant sites. Urokinase-type plasminogen activators (uPA) and plasminogen activator inhibitor type 1, mRNAs accumulate in atypical nevocytes and in melanoma cells, but not in benign nevocytes. The protein sequence is known in the art and publicly available, for example GeneBank accession number NM_002658, NM_000602. Description of the protein may be found in, for example, Delbaldo, Masouye, Saurat, Vassalli and Sappino, 1994, Cancer Res, 54, 4547-52 herein specifically incorporated by reference with respect to the teaching of the protein.

Cathepsins (B, D, H, L) are of interest as markers. The proteases cathepsin B and L are increased in all melanocytic lesions, and the corresponding mRNA levels were elevated only in melanomas. Cathepsin D protein and mRNA were expressed to a higher degree only in the dysplastic nevus and in melanomas. Cathepsin H activity, immunoreactivity, and mRNA are correlated inversely with the invasive potential of the lesion. The protein sequence is known in the art and publicly available, for example GeneBank accession number NM_007798, NM_009983, NM_007801, NM_001912. Description of the proteins may be found in, for example, Frohlich, Schlagenhauff, Mohrle, Weber, Klessen and Rassner, 2001, Cancer, 91, 972-82 herein specifically incorporated by reference with respect to the teaching of the proteins.

In some embodiments, the probe is an antibody or fragment thereof. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The term includes monoclonal antibodies, multispecific antibodies (antibodies that include more than one domain specificity), human antibody, humanized antibody, and antibody fragments with the desired biological activity.

Polyclonal antibodies can be raised by a standard protocol by injecting a production animal with an antigenic composition, formulated as described above. See, e.g., Harlow and Lane, Antibodies: A Laboratory Manual, Cold Spring Harbor Laboratory, 1988. In one such technique, a Class II target antigen comprising an antigenic portion of the polypeptide is initially injected into any of a wide variety of mammals (e.g., mice, rats, rabbits, sheep or goats). When utilizing an entire protein, or a larger section of the protein, antibodies may be raised by immunizing the production animal with the protein and a suitable adjuvant (e.g., Freund's, Freund's complete, oil-in-water emulsions, etc.) Alternatively, for monoclonal antibodies, hybridomas may be formed by isolating the stimulated immune cells, such as those from the spleen of the inoculated animal. These cells are then fused to immortalized cells, such as myeloma cells or transformed cells, which are capable of replicating indefinitely in cell culture, thereby producing an immortal, immunoglobulin-secreting cell line.

In addition, the antibodies or antigen binding fragments may be produced by genetic engineering. In this technique, as with the standard hybridoma procedure, antibody-producing cells are sensitized to the desired antigen or immunogen. The messenger RNA isolated from the immune spleen cells or hybridomas is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones, which co-express a heavy and light chain (resembling the Fab fragment or antigen binding fragment of an antibody molecule). The vectors that carry these genes are co-transfected into a host (e.g. bacteria, insect cells, mammalian cells, or other suitable protein production host cell). When antibody gene synthesis is induced in the transfected host, the heavy and light chain proteins self-assemble to produce active antibodies that can be detected by screening with the antigen or immunogen.

Antibody fragments that recognize specific epitopes may be generated by techniques well known in the field. These fragments include, without limitation, F(ab')$_2$ fragments, which can be produced by pepsin digestion of the antibody molecule, and Fab fragments, which can be generated by reducing the disulfide bridges of the F(ab')$_2$ fragments. Alternatively, single chain antibodies (Fv, as described below) can be produced from phage libraries containing human variable regions.

In addition to entire immunoglobulins (or their recombinant counterparts), immunoglobulin fragments comprising the epitope binding site (e.g., Fab', F(ab')$_2$, or other fragments) are useful as antibody moieties in the present invention. Such antibody fragments may be generated from whole immunoglobulins by ficin, pepsin, papain, or other protease cleavage. "Fragment," or minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif).

Candidate antibodies can be tested for by any suitable standard means, e.g. ELISA assays, etc. As a first screen, the antibodies may be tested for binding against the immunogen. After selective binding is established, the candidate antibody may be tested for appropriate activity in an in vivo model. In a preferred embodiment, antibody compounds may be screened using a variety of methods in vitro and in vivo. These methods include, but are not limited to, methods that measure binding affinity to a target, and biodistribution of the compound within an animal or cell. These and other screening methods known in the art provide information on the ability of a compound to bind to, modulate, or otherwise interact with the specified target and are a measure of the compound's efficacy.

In another embodiment, the probe is a peptide consisting of 3 to 50 aminoacids. Peptides of interest include peptides that specifically bind to integrins, e.g. integrins on the surface of tumor cells or angiogenic vessels found adjacent to tumor cell growth. In one embodiment, the peptide comprises an RGD sequence or variations thereof. The peptide that contains the RGD motive may be linear or circular, for example as shown in Table 1. An example of a RGD peptide is CDCRGDCFC (SEQ ID NO: 1). Cyclic RGD peptide can be synthesized as published (Wang, McMurray, Wu, Campbell and Li, 2005, Cancer Biother Radiopharm, 20, 547-56).

Topical compositions comprise an effective dose of a probe according to the invention, and a dermatologically acceptable vehicle. The dose present in a topical composition may be at least about 0.1 mM, at least about 1 μM, at least about 10 μM, at least about 100 μM, at least about 1 mM, at least about 10

TABLE 1

| Compound | $IC_{50}$ $\alpha v\beta 3$ (nm) | Tumour model | Tumour uptake (% ID/g) | Tumour/ muscle | Tumour/ blood |
|---|---|---|---|---|---|
| c(RGDy V) | 10 | Osteo | $1.5 \pm 0.2^b$ | 4.9 | 8.6 |
| c(RGDfY) | 40 | Osteo | $0.4 \pm 0.1^c$ | 2.7 | 1.1 |
| RGD | 40 | M21 | $1.8 \pm 0.3^b$ | 6.2 | 7.9 |
| c(RGDfMe V) | 1 | DLD-1 | $0.9 \pm 0.1^c$ | 2.7 | 5.2 |
| DKCK-RGD | — | M21 | $1.1 \pm 0.1^b$ | 8.1 | 9.7 |
| DOTA-RGD | — | Osteo | $1.1 \pm 0.04^c$ | 2.8 | 11.8 |
| DTPA-RGD | — | CA20948 | $0.1 \pm 0.02^d$ | 7.9 | 9.2 |
| RGD-4C | $7,000^f$ | ACHN | $0.6 \pm 0.1^e$ | 2.6 | 1.6 |
| DOTA-E-[c(RGDfK)]$_2$ | — | OVCAR-3 | $7.5 \pm 1.5^b$ | — | $40^g$ |
| HYNIC-E-[c(RGDfK)]$_2$ | — | OVCAR-3 | $5.8 \pm 0.5^b$ | — | $10^g$ |
| c(RGDyK) | — | MDA-MB | $3.0 \pm 0.1^b$ | 4.7 | 20.2 |
| mPEG-c(RGDyK) | — | U87MG | $5.1 \pm 0.3^b$ | — | 85 |
| FB-c(RGDyK) | — | MDA-MB | $1.0 \pm 0.3^b$ | 5.8 | 12.2 |
| DOTA-c(RGDyK) | — | MDA-MB | $1.4 \pm 0.1^b$ | 6 | 6.9 |
| FP-PEG-c(RGDyK) | — | U87MG | $2.6 \pm 0.1^b$ | 25.6 | 18.4 |
| DOTA-PEG-c(RGDyK) | — | U87MG | $1.6 \pm 0.2^d$ | $16^g$ | $80^g$ |
| DOTA-E[E-c(RGDyK)z]$_2$ | $48^h$ | U87MG | $7.6 \pm 0.6^b$ | $12^g$ | $36^g$ |
| FP-E-c(RGDyK)$_2$ | — | MDA-MB | $4^{b,g}$ | — | — |
| c(RGDfE)HEG-Dpr | $20^i$ | M21 | $0.5 \pm 0.1^b$ | 13.2 | 12.4 |
| (c(RGDfE)HEG)$_2$-K-Dpr | $3^j$ | M21 | $1.6 \pm 0.1^b$ | 14.2 | 12.4 |
| ((c(RGDfE)HEG)$_2$-K)$_2$-Dpr | $0.2^j$ | M21 | $1.7 \pm 0.1^b$ | 23.1 | 21.3 |

$^a$Osteo murine osteosarcoma, M21 human melanoma, DLD-1 human colon adenocarcinoma, CA20948 rat pancreatic tumour, ACHN human renal adenocarcinoma, OVCAR-3 ovarian carcinoma, MDA-MB human breast cancer, U87MG human glioblastoma
$^b$120 min p.i.;
$^c$60 min p.i.;
$^d$4 h p.i.;
$^e$6 h p.i.
$^f$Association constant is given here
$^g$Estimated from graphical presentations
$^i$IC$_{50}$ value for the corresponding compound A detectable label is linked to them probe, which may be directly or indirectly detectable, preferably directly detectable. Fluorescent labels of interest include: fluorescein, rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), the cyanine dyes, such as Cy3, Cy5, Cy 5.5, Alexa 542, Alexa 647, Alexa 680, Alexa 700, Bodipy 630/650, fluorescent particles, fluorescent semiconductor nanocrystals, and the like. The labeled probes can be produced using any convenient protocol. The labeled probes may be a combination of more than one peptide or protein or protein fragments. The detectable label may exhibit fluorescence resonance energy transfer when a donor fluorescent protein moiety is excited, and transfers detectable fluorescence to an acceptor fluorescent protein.

In some embodiments, the wavelength for emission from the label is in the range of the near infra red. Such labels include, without limitation, Alexa 647, Alexa 680, Alexa 700 and Cy5.5. Characteristics considered for label selection include its light absorption, and a minimization of autofluorescence from the body surface to be measured. The probe will respond to florescent illumination of a specific wavelength and will then emit light at a different wavelength.

mM. The probe will be available as an application unit and applied directly on to the skin in the form of a gel, cream, spray or ointment.

A typical dose for a topical formulation is from about 1 μl to about 100 μl to about 1 ml, to about 10 ml, applied in a lotion, cream, gel, etc. to the affected skin. In use, a small quantity of the composition is applied to exposed areas of the skin, from a suitable container or applicator and, if necessary, it is then spread over and/or rubbed into the skin using the hand or fingers or a suitable device.

In some embodiments, the topical formulation comprises skin penetration enhancers. Such enhancers reversibly decrease skin barrier resistance, and include without limitation, sulphoxides (such as dimethylsulphoxide, DMSO), azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes.

Dimethyl sulfoxide (DMSO) is of particular interest as a penetration enhancer. It is a powerful aprotic solvent that hydrogen bonds with itself rather than with water; it is colorless, odorless and is hygroscopic and is often used in many areas of pharmaceutical sciences as a solvent (Williams and Barry, 2004, Ads Drug Deliv Rev, 56, 603-18). DMSO as a as a skin penetration agent is used in concentrations varying from 5-99%, gels containing 10% DMSO have shown best skin permeation (Baboota, Shakeel and Kohli, 2006, Methods Find Exp Clin Pharmacol, 28, 109-14). Formulations of interest may comprise at least about 5% DMSO, at least about 10% DMSO, at least about 25% DMSO, at least about 35% DMSO, at least about 50% DMSO, at least about 60% DMSO, at least about 75% DMSO, at least about 85% DMSO, at least about 95% DMSO, at least about 99% DMSO, usually calculated as volume/volume.

Conditions for Diagnosis

Basal cell carcinoma is the most common type of skin cancer, with >400,000 new cases yearly in the USA. It is more common in fair-skinned, sun-exposed persons. The clinical presentation and biologic behavior of basal cell carcinomas are highly variable. They may appear as small, shiny, firm, almost translucent nodules; ulcerated, crusted papules or nodules; flat, scarlike indurated plaques; or red, marginated, thin papules or plaques difficult to differentiate from psoriasis or localized dermatitis. Most commonly the carcinoma begins as a shiny papule, enlarges slowly, and, after a few months or years, shows a shiny, pearly border with prominent engorged vessels (telangiectases) on the surface and a central dell or ulcer. Recurrent crusting or bleeding is not unusual, and the lesion continues to enlarge slowly. Commonly, the carcinomas may alternately crust and heal, which may decrease the patient's and physician's concern about the importance of the lesion. Basal cell carcinomas rarely metastasize but may invade healthy tissues. Rarely, death may ensue because the carcinoma invades or impinges on underlying vital structures or orifices (eyes, ears, mouth, bone, dura mater).

Squamous cell carcinoma, the second most common type of skin cancer, may develop in normal tissue, in a preexisting actinic keratosis or patch of leukoplakia, or in burn scars. The incidence in the USA is 80,000 to 100,000 cases annually. The clinical appearance is highly variable. The tumor may begin as a red papule or plaque with a scaly or crusted surface and may become nodular, sometimes with a warty surface. In some, the bulk of the lesion may lie below the level of the surrounding skin. Eventually it ulcerates and invades the underlying tissue. The percentage of squamous cell carcinomas on sun-exposed skin that metastasize is quite low. However, about ⅓ of lingual or mucosal cancers have metastasized before diagnosis. A biopsy is essential. In general, the prognosis for small lesions removed early and adequately is excellent. Treatment is the same as for basal cell carcinoma.

Malignant melanoma is a malignant melanocytic tumor arising in a pigmented area: skin, mucous membranes, eyes, and CNS. About 25,000 new cases of malignant melanoma occur yearly in the USA, causing about 6000 deaths. The incidence is rising rapidly. Sun exposure is a risk, as is family history and the occurrence of lentigo maligna, large congenital melanocytic nevus, and the dysplastic nevus syndrome. Malignant melanomas vary in size, shape, and color (usually pigmented) and in their propensity to invade and metastasize. This neoplasm may spread rapidly, causing death within months of its recognition, yet the 5-yr cure rate of early, very superficial lesions is nearly 100%. Thus, cure depends on early diagnosis and early treatment.

Lentigo maligna melanoma arises from lentigo maligna; it appears on the face or other sun-exposed areas usually in elderly patients as an asymptomatic, 2- to 6-cm, flat, tan or brown, irregularly shaped macule or patch with darker brown or black spots scattered irregularly on its surface. In lentigo maligna, both normal and malignant melanocytes are confined to the epidermis; when malignant melanocytes invade the (dermis, the lesion is called lentigo maligna melanoma and the cancer may metastasize.

Superficial spreading melanoma accounts for ⅔ of malignant melanomas. Usually asymptomatic, it is usually diagnosed when smaller than lentigo maligna melanoma and occurs most commonly on women's legs and men's torsos. The lesion is usually a plaque with irregular raised, indurated tan or brown areas, which often show red, white, black, and blue spots or small, sometimes protuberant, blue-black nodules. Small notchlike indentations of the margins may be noted, along with enlargement or color change. Histologically, atypical melanocytes characteristically invade dermis and epidermis.

Nodular melanoma constitutes 10 to 15% of malignant melanomas. It may occur anywhere on the body as a dark, protuberant papule or a plaque that varies from pearl to gray to black. Occasionally, a lesion contains little if any pigment or may look like a vascular neoplasm. Unless it ulcerates, nodular melanoma is asymptomatic, but the patient usually seeks advice because the lesion enlarges rapidly.

Acral-lentiginous melanoma arises on palmar, plantar, and subungual skin and has a characteristic histologic picture similar to lentigo maligna melanoma.

For treatment of such skin cancers, topical or intra-lesional treatment with granulysin peptides may be combined with surgery, irradiation (e.g. in combination with aminolevulinic acid, psoralens, etc.), and/or chemotherapy, e.g. treatment with 5-fluorouracil, cisplatin, etc. Treatment will be performed at a dose and for a length of time sufficient to reduce the number of transformed cells present in the lesion. This reduction will typically last at least 2 but preferably 3 or more months, or even 4 to 6 or more months, but most preferably a year or longer, either while treatment is continued or after it is stopped. Therapy with granulysin in a combined therapy will generally provide for enhanced efficacy relative to monotherapy.

Benign Skin Growths

Benign skin growths include moles, warts, etc. Moles are circumscribed pigmented macules, papules, or nodules composed of clusters of melanocytes or nevus cells. They may be small or large; flesh-colored, yellow-brown, or black; flat or raised; smooth, hairy, or warty; broad-based or pedunculated. Moles can be removed or cosmetic purposes. Dysplastic nevi are pigmented lesions, often rather large, with borders that are usually irregular and ill-defined, with variegated colors usually of brown and tan tones, and with macular or papular components. Seborrheic Warts are pigmented superficial epithelial lesions that are usually warty but may occur as smooth papules. Seborrheic keratoses vary in size and grow slowly. They may be round or oval or flesh-colored, brown, or black; usually appear "stuck on"; and may have a verrucous, velvety, waxy, scaling, or crusted surface. They are not premalignant and need no treatment unless they are irritated, itchy, or cosmetically bothersome. Keratoacanthoma is a round, firm, usually flesh-colored nodule with sharply sloping borders and a characteristic central crater containing keratinous material. Onset is rapid; usually within 1 or 2 mo the lesion reaches its full size, which may be >5 cm. Common sites are sun-exposed areas, the face, the forearm, and the dorsum of the hand.

Detection Methods and Device

For imaging of lesions suspected of neoplasia in the skin, a probe of the invention is topically applied to the region of interest, where a region may be from around about 0.1 cm in diameter to about 5 cm in diameter. The region of interest is cleaned, e.g. with alcohol, mild detergent, etc. One, two or more lesions may be prepared at the same time for parallel analysis, or in sequence. A formulation comprising the probe or probes is applied to the area, in an amount sufficient for detection. The probe is allowed to incubate for a period of time sufficient for transdermal penetration and localization at regions of neoplasia. The surface of the skin is rinsed of excess probe, e.g. with alcohol, mild detergent, water, etc. The region of interest is now ready to be detected by imaging and analyzed.

The detection device may be provided in various configurations. In one embodiment, a home detection device is provided, wherein a user can acquire fluorescent images of a lesion with a single use, flexible image acquisition device as shown in FIG. 1.

In an alternative embodiment, for example as shown in FIG. 5, the detection unit may utilizes a "reusable" image acquisition device. The system enables the acquisition of several images on the surface of the body. LED body coordinate markers and lesion markers may position the lesion on the patient's body for long time tracking of lesion to determine progression of changes in specific lesions.

The method of operating the flexible image acquisition device will occur as follows after the application of the probe to the area of investigation and the appropriate time post application of the probe to permit specific binding of the probe and the dispersal of the unbound probe. The image acquisition unit is placed over the illumination unit and the image acquisition unit and the illumination unit is placed above the lesion of interest. The adhesion material is then secured around the device to prevent outside light to contaminate the specific light. The opaque sheet between the camera and the illumination device is pulled out and exposure is initiated by pressing a button on the electronic timer on the illumination source. 6. When the exposure is completed the instant film will be pulled out and passed through the film pulling device. 7. The image is allowed to develop. 8. The image is now ready for inspection to determine light emission from the probe and the presence of neoplastic cells.

The second module is targeted for the use of professional health care individuals. This module comprises 2 parts: a digital imaging system (51-56); and optionally, a mapping device to map the lesion on the body coordinates (61-64).

The reusable imaging device may be operated in the following manner; the probe is applied to the area of investigation. The image acquisition device is placed over the area of investigation; the light beam will shine from the illumination box (51) through the fiber bundle (52) and the excitation filter in the florescence cube (53). The light is then reflected by a semi transparent mirror in the cube towards the area of investigation. The light reaches the surface of investigation and will excite the fluorophore attached to the probe that will emit light in its specific emission wave length. The light emitted from the body surface returns to the filter cube and passed the emission filter to reach the image acquisition device. The image can be transferred to the data recording device for display and analysis. When the emission and excitation filters are removed from the optical path the camera may take bright field images where the lamp in the illumination cube 51 can serve as white light illumination.

The mapping device may be used in the following way. During the process of image acquisition of the fluorescence emitted from the bound probe on the body surface under investigation, the LED markers are placed on distinct and defined points of the body under investigation. The lesion marker will mark the location of the lesion. The image acquisition device will acquire an image of the patient with the led markers on his body and the laser marker indicating the position of the lesion. The image from the image acquisition device is transferred to a data recording device that will display, store and analyze the data and with a specific software or hardware program. The analysis will contain the probability and specificity of the binding of the probe while recording the lesion position on the body coordinates. This will generate a bank of images and coordinates to create a computerized map of the lesions on the whole body with image of the probe binding and bright field image for every lesion inspected on the patient body.

The individual/customer can be instructed to place the image from the image detection device in an envelope and mail it to a diagnostic lab, for example, using provided prepaid envelope. In the laboratory the image can be analyzed by a pathologist to make the diagnosis for the potential presence or absence of neoplastic tissue/cells in the image. A written result report can be faxed/mailed to the individual and/or clinician in charge of the individual/customer or send to the computerized, telephone or Internet report system. The individual/customer can then have the opportunity to obtain the diagnosis and medical recommendation message over the phone (or internet) using his identification number. The specimen processing system offers opportunity for automatization. Trained technicians may also prescreen the images.

Additional Embodiments of Device

When the device is not assembled or not in use, the opening of the device can be closed with the aid of a dummy which essentially matches the outer form of the measurement device, and therefore acts as a closure. It is thus possible to protect components of the device from damaging influences (contamination, etc.) during a period when the device is not in use.

What is claimed is:

1. A non-invasive method for analysis of a skin lesion of an individual for the presence of a melanoma having a Breslow thickness of less than one millimeter, the method comprising:
topically contacting a region of skin of the individual comprising the skin lesion with a formulation comprising an effective concentration of an RGD peptide comprising a detectable label, which peptide specifically binds to an integrin, wherein the peptide is provided in a topical formulation containing a skin penetration enhancer selected from the group consisting of a sulphoxide, azone, pyrrolidone, alcohol, glycol, surfactant, and terpene;
incubating the formulation on the region of skin for a period of time sufficient for transdermal penetration of the peptide and localization of the peptide to a region of the skin lesion if the integrin is present;
illuminating the region of skin with light at a wavelength appropriate for image acquisition;
generating an image of localization of the peptide in the region of skin;
wherein localization of the peptide to the region of the skin lesion is indicative of melanoma.

2. The method of claim 1, wherein the skin penetration enhancer is selected from the group consisting of dimethylsulfoxide (DMSO), laurocapram, 2-pyrrolidone (2P), ethanol and propylene glycol.

3. The method of claim 2, wherein the skin penetration enhancer is DMSO.

4. The method of claim 1, wherein the image of localization is generated within a period of several minutes to one hour.

5. The method of claim 1, wherein the effective concentration of the RGD peptide is from 0.1 μM to 10 mM.

6. The method of claim 1, wherein the integrin is integrin $\alpha v \beta 3$.

7. The method of claim 1, wherein the integrin is integrin $\alpha 5 \beta 1$.

8. The method of claim 1, wherein the detectable label comprises a fluorescent label.

9. The method of claim 1, wherein the RGD peptide consists of SEQ ID NO: 1.

10. The method of claim 1, wherein the melanoma is selected from the group consisting of malignant melanoma, lentigo maligna melanoma, nodular melanoma, a superficial spreading melanoma, and acral-lentiginous melanoma.

11. The method of claim 1, further comprising providing a diagnosis to the individual as having melanoma based on the localization of the peptide to the region of the skin legion.

12. The method of claim 1, wherein the integrin is on the surface of a tumor cell of the melanoma.

13. The method of claim 1, wherein the integrin is on the surface of an angiogenic vessel found adjacent to a tumor cell of the melanoma.

14. The method of claim 1, wherein the RGD peptide consists of 3 to 50 amino acids.

15. The method of claim 1, wherein the formulation contacted to the region of skin is from about 1 μl to about 10 mL in volume.

16. The method of claim 1, further comprising washing the skin legion after the incubating.

17. The method of claim 16, wherein the washing removes an excess of the peptide on the skin legion, wherein the excess is not bound to the integrin.

* * * * *

UNITED STATES PATENT AND TRADEMARK OFFICE
CERTIFICATE OF CORRECTION

PATENT NO. : 8,642,009 B2
APPLICATION NO. : 12/097509
DATED : February 4, 2014
INVENTOR(S) : Shachaf et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 584 days.

Signed and Sealed this
Eleventh Day of August, 2015

Michelle K. Lee
*Director of the United States Patent and Trademark Office*